United States Patent
Nakagawa et al.

(10) Patent No.: US 12,359,233 B2
(45) Date of Patent: Jul. 15, 2025

(54) PRODUCTION METHOD OF (R)-RETICULINE

(71) Applicant: Fermelanta, Inc., Nonoichi (JP)

(72) Inventors: Akira Nakagawa, Nonoichi (JP); Hiromichi Minami, Nonoichi (JP)

(73) Assignee: Fermelanta, Inc., Ishikawa (JP)

(*) Notice: Subject to any disclaimer, the term of this patent is extended or adjusted under 35 U.S.C. 154(b) by 554 days.

(21) Appl. No.: 17/622,288

(22) PCT Filed: Jun. 16, 2020

(86) PCT No.: PCT/JP2020/023561
§ 371 (c)(1),
(2) Date: Dec. 23, 2021

(87) PCT Pub. No.: WO2020/262107
PCT Pub. Date: Dec. 30, 2020

(65) Prior Publication Data
US 2022/0251615 A1 Aug. 11, 2022

(30) Foreign Application Priority Data
Jun. 24, 2019 (JP) .................... 2019-116701

(51) Int. Cl.
| | |
|---|---|
| *C12P 17/12* | (2006.01) |
| *C12N 1/20* | (2006.01) |
| *C12N 9/02* | (2006.01) |
| *C12N 9/10* | (2006.01) |
| *C12N 15/52* | (2006.01) |
| *C12N 15/70* | (2006.01) |

(52) U.S. Cl.
CPC .............. *C12P 17/12* (2013.01); *C12N 1/20* (2013.01); *C12N 9/0042* (2013.01); *C12N 9/0071* (2013.01); *C12N 9/1029* (2013.01); *C12N 15/52* (2013.01); *C12N 15/70* (2013.01); *C12Y 106/02004* (2013.01); *C12Y 114/19* (2013.01); *C12Y 203/01037* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 11,124,814 B2* | 9/2021 | Siddiqui | C12N 9/0071 |
| 2008/0176754 A1* | 7/2008 | Smolke | C12P 7/24 |
| | | | 506/4 |
| 2018/0078100 A1 | 3/2018 | Bates et al. | |

FOREIGN PATENT DOCUMENTS

| | | |
|---|---|---|
| JP | 2017-500024 A | 1/2017 |
| WO | 2012/039438 A1 | 3/2012 |
| WO | 2015/081437 A1 | 6/2015 |
| WO | 2015/173590 A1 | 11/2015 |
| WO | 2016/207643 A1 | 12/2016 |

OTHER PUBLICATIONS

International Preliminary Report on Patentability and Written Opinion issued in corresponding International Patent Application No. PCT/JP2020/023561 dated Jan. 6, 2022.
International Search Report issued in corresponding International Patent Application No. PCT/JP2020/023561 dated Sep. 1, 2020.
Nakagawa et. al., "A bacterial platform for fermentative production of plant alkaloids," Nature Communications, 2: 326 (2011).
Winzer et al., "Morphinan biosynthesis in opium poppy requires a P450-oxidoreductase fusion protein," Science, 349: 309-312 (2015).
Nakagawa et al., "Total biosynthesis of opiates by stepwise fermentation using engineered *Escherichia coli*," Nature Communications, 7: 10390 (2016).

* cited by examiner

*Primary Examiner* — Blaine Lankford
(74) *Attorney, Agent, or Firm* — Morgan, Lewis & Bockius LLP

(57) ABSTRACT

The present invention relates to a production method of (R)-reticuline including: a step for obtaining a recombinant host cell by inserting, into a host cell, a gene 1 which is composed of a nucleotide sequence having at least 70% homology to a nucleotide sequence of SEQ ID NO: 2 and which is DNA encoding a protein having an enzymatic activity of CYP80Y2, and a gene 2 which is composed of a nucleotide sequence having at least 70% homology to a nucleotide sequence of SEQ ID NO: 3 and which is DNA encoding a protein having an enzymatic activity of oxidoreductase; a step for expressing, in the recombinant host cell, the protein having the enzymatic activity of CYP80Y2 and the protein having the enzymatic activity of oxidoreductase; and a step for producing (R)-reticuline from (S)-reticuline by using the recombinant host cell.

10 Claims, 3 Drawing Sheets
Specification includes a Sequence Listing.

(a)

(b)

_US 12,359,233 B2_

PRODUCTION METHOD OF (R)-RETICULINE

SEQUENCE LISTING SUBMISSION VIA EFS-WEB

A computer readable text file, entitled "SequenceListing.txt" created on Dec. 21, 2021 with a file size of 28,459 bytes contains the sequence listing for this application and is hereby incorporated by reference in its entirety.

TECHNICAL FIELD

The present invention relates to a production method of (R)-reticuline, which is a plant benzylisoquinoline alkaloid.

BACKGROUND ART

Opioid analgesics such as morphine are known as pharmaceutically useful compounds belonging to benzylisoquinoline alkaloids. Conventionally, opioid analgesics have been produced by a method of extraction from natural plants. Analgesics obtained by this method utilizing secondary metabolites of plants are more expensive than analgesics produced by other methods, and thus, another method has been desired.

Some benzylisoquinoline alkaloids, including morphine, can also be totally synthesized by chemical synthesis. However, due to the complex structure and chirality of alkaloids, it is difficult to produce these benzylisoquinoline alkaloids at low cost.

Therefore, the present inventors have attempted to carry out the whole biosynthesis process of benzylisoquinoline alkaloids in a microbiological system (Patent Literature 1 and Non-Patent Literature 1 and 2). This method, which uses microorganisms as host cells, combines plant and microbial enzymes to reconstruct the isoquinoline alkaloid biosynthetic pathway.

Incidentally, benzylisoquinoline alkaloids are synthesized from tyrosine in many plant species such as Magnoliaceae, Ranunculaceae, Berberidaceae, Papaveraceae, and others, and most of these plant species have (S)-reticuline as a biosynthetic intermediate.

Thebaine, which is a raw material for opioid analgesics, is obtained through a reaction in which (S)-reticuline is converted to the optical isomer (R)-reticuline. The enzyme that converts (S)-reticuline to (R)-reticuline had not been identified for a long time, but in Non-Patent Literature 3, a STORR ((S)-to-(R)-reticuline) protein, which is an enzyme that converts (S)-reticuline to (R)-reticuline, was identified (Non-Patent Literature 3).

CITATION LIST

Patent Literature

[Patent Literature 1] International Publication No. WO 2012/039438
[Patent Literature 2] Japanese Unexamined Patent Publication No. 2017-500024
[Non-Patent Literature 1] Akira N, et al. (2016) Total biosynthesis of opiates by stepwise fermentation using engineered *Escherichia coli*. Nat Commun. 7: 10390
[Non-Patent Literature 2] Akira N, et al. (2011) A bacterial platform for fermentative production of plant alkaloids. Nat Commun. 2: 326
[Non-Patent Literature 3] Thilo W, et al. (2015) Morphinan biosynthesis in opium poppy requires a P450-oxidoreductase fusion protein. Science. 349 (6245): 309-312

SUMMARY OF INVENTION

Technical Problem

However, Non-Patent Literature 3 does not disclose a specific method for producing (R)-reticuline from (S)-reticuline using a microorganism.

On the other hand, Patent Literature 2 discloses a method for producing (R)-reticuline using a eukaryote such as yeast as a host cell and using the same or similar amino acid sequence as STORR (Patent Literature 2).

However, Patent Literature 2 does not disclose a method for producing (R)-reticuline using a prokaryote as a host cell. This is because it is difficult to functionally express the P450 enzyme and the salutaridine synthase (SalS) in prokaryotes. Therefore, in Patent Literature 2, the target applicable as a host cell remains in eukaryotes such as yeast, and it is difficult to produce (R)-reticuline using a prokaryote (for example, *Escherichia coli*) as a host cell.

Further, in Patent Literature 2, (S)-reticuline is also mixed with the produced (R)-reticuline, and it is difficult to generate only (R)-reticuline. Therefore, in the method of Patent Literature 2, in order to obtain only (R)-reticuline, it is necessary to perform optical resolution by a chiral column or the like.

Therefore, an object of the present invention is to provide a method for producing (R)-reticuline from (S)-reticuline with high conversion efficiency. Another object of the present invention is to provide a method capable of producing (R)-reticuline with high conversion efficiency even when a prokaryote is used as a host cell. Still another object of the present invention is to supply an inexpensive opioid analgesic by constructing a thebaine production system applicable to *Escherichia coli*, which is a practically useful prokaryote.

Solution to Problem

The present inventor has found that (R)-reticuline can be obtained with extremely high conversion efficiency by adopting the method of the present invention with respect to the above-described problems. It was also found that the method of the present invention can produce (R)-reticuline with extremely high conversion efficiency even when a prokaryote is used as a host cell. In the method of the present invention, the final amount of (S)-reticuline was able to be made an amount equal to or lower than the detection limit, and the proportion of produced (R)-reticuline was apparently 100% of the total amount of reticuline.

According to an aspect of the present invention, there is provided a production method of (R)-reticuline including: a step for obtaining a recombinant host cell by inserting, into a host cell, a gene 1 (hereinafter, also referred to as "gene encoding CYP80Y2") which is composed of a nucleotide sequence having at least 70% homology to a nucleotide sequence of SEQ ID NO: 2 and which is DNA encoding a protein having an enzymatic activity of CYP80Y2, and a gene 2 (hereinafter, also referred to as a "gene encoding oxidoreductase") which is composed of a nucleotide sequence having at least 70% homology to a nucleotide sequence of SEQ ID NO: 3 and which is DNA encoding a protein having an enzymatic activity of oxidoreductase; a step for expressing, in the recombinant host cell, the protein having the enzymatic activity of CYP80Y2 and the protein having the enzymatic activity of oxidoreductase; and a step for producing (R)-reticuline from (S)-reticuline by using the recombinant host cell.

According to another aspect of the present invention, there is provided a production method of (R)-reticuline including: a step for dividing a gene 3 (hereinafter, also referred to as "gene encoding STORR") which is composed of a nucleotide sequence having at least 70% homology to a nucleotide sequence of SEQ ID NO: 1 and which is DNA encoding a protein having an enzymatic activity of STORR into a gene 1 which is composed of a nucleotide sequence having at least 70% homology to a nucleotide sequence of SEQ ID NO: 2 and which is DNA encoding a protein having an enzymatic activity of CYP80Y2, and a gene 2 which is composed of a nucleotide sequence having at least 70% homology to a nucleotide sequence of SEQ ID NO: 3 and which is DNA encoding a protein having an enzymatic activity of oxidoreductase; a step for obtaining a recombinant host cell by inserting the gene 1 and the gene 2 into a host cell; a step for expressing, in the recombinant host cell, the protein having the enzymatic activity of CYP80Y2 and the protein having the enzymatic activity of oxidoreductase; and a step for producing (R)-reticuline from (S)-reticuline by using the recombinant host cell.

According to the above-described production method of (R)-reticuline of the present invention, (R)-reticuline can be obtained with extremely high conversion efficiency.

In the above-described production method of (R)-reticuline according to the present invention, at least one of steps may further be provided among a step for deleting the nucleotide sequence encoding an N-terminal hydrophobic region of the protein having the enzymatic activity of CYP80Y2 from the gene 1, a step for expressing a protein having an enzymatic activity of 5-aminolevulinate synthase 1 by introducing, into the host cell, a gene 4 (hereinafter, also referred to as "gene encoding 5-aminolevulinate synthase 1") which is composed of a nucleotide sequence having at least 70% homology to a nucleotide sequence of SEQ ID NO: 4 and which is DNA encoding the protein having an enzymatic activity of 5-aminolevulinate synthase 1, and a step for expressing the protein having an enzymatic activity of CPR by introducing, into the host cell, a gene 5 (hereinafter, also referred to as "gene encoding CPR") which is composed of a nucleotide sequence having at least 70% homology to a nucleotide sequence of SEQ ID NO: 5 and which is DNA encoding the protein having the enzymatic activity of CPR. Accordingly, (R)-reticuline can be efficiently produced even in a case where a prokaryote is used as a host cell.

In the aspect, in the above-described production method of (R)-reticuline according to the present invention, a step for deleting the nucleotide sequence encoding an N-terminal hydrophobic region of the protein having the enzymatic activity of CYP80Y2 from the gene 1; a step for expressing a protein having an enzymatic activity of 5-aminolevulinate synthase 1 by introducing, into the host cell, a gene 4 which is composed of a nucleotide sequence having at least 70% homology to a nucleotide sequence of SEQ ID NO: 4 and which is DNA encoding the protein having an enzymatic activity of 5-aminolevulinate synthase 1; and a step for expressing a protein having an enzymatic activity of CPR by introducing, into the host cell, a gene 5 which is composed of a nucleotide sequence having at least 70% homology to a nucleotide sequence of SEQ ID NO: 5 and which is DNA encoding the protein having the enzymatic activity of CPR, may further be provided. Accordingly, (R)-reticuline can be produced even more efficiently even in a case where a prokaryote is used as a host cell.

In the production method of (R)-reticuline according to the present invention, the host cell may be a prokaryote.

In the production method of (R)-reticuline according to the present invention, the prokaryote may be *Escherichia coli*.

According to the production method of the present invention, the final amount of (S)-reticuline becomes equal to or less than the detection limit, and the proportion of produced (R)-reticuline is apparently 100% of the total amount of reticuline.

The production method of the present invention can produce (R)-reticuline with extremely high conversion efficiency as described above even when a prokaryote is used as a host cell. Therefore, the production method of the present invention is practically useful because, for example, *Escherichia coli*, which is a prokaryote, can be applied as a host cell to produce (R)-reticuline.

Advantageous Effects of Invention

According to the present invention, it is possible to provide a method for producing (R)-reticuline from (S)-reticuline with extremely high conversion efficiency. In the production method of the present invention, the final amount of (S)-reticuline can be made an amount which is equal to or less than the detection limit Therefore, in the production method of the present invention, it is not necessary to perform a process (optical resolution or the like) for obtaining only (R)-reticuline. Further, the production method of the present invention can produce (R)-reticuline with extremely high conversion efficiency as described above even when a prokaryote is used as a host cell. Therefore, according to the present invention, for example, it is possible to construct a thebaine production system applicable to *Escherichia coli*, which is a practically useful prokaryote. Accordingly, mass production of (R)-reticuline is also possible, and thus, it is possible to supply inexpensive opioid analgesics.

DESCRIPTION OF EMBODIMENTS

Figure 1:
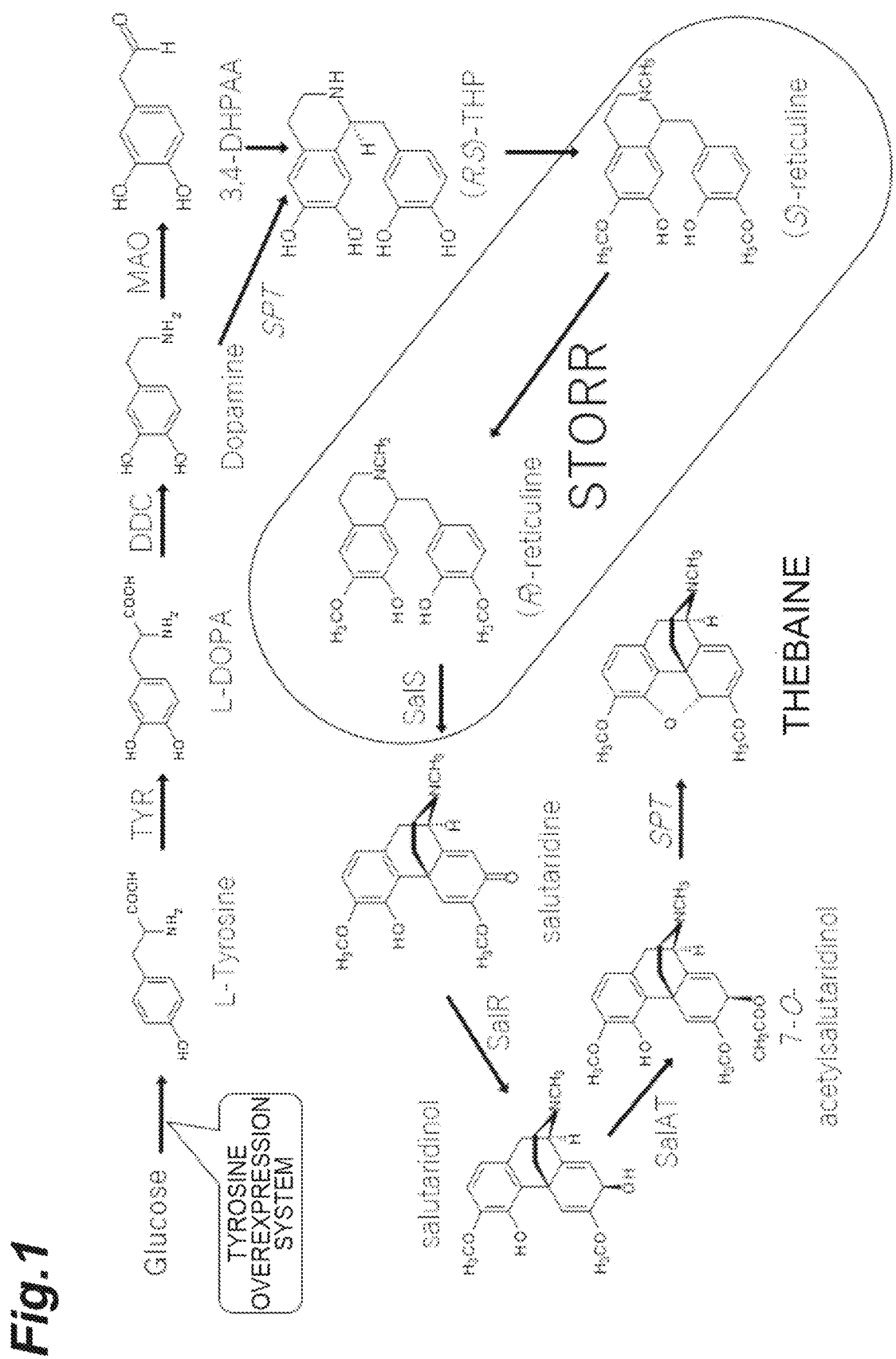
FIG. 1 shows a biosynthetic pathway of (R)-reticuline reconstructed in a host cell in the present invention.

Hereinafter, embodiments for carrying out the present invention will be described in detail. However, the present invention is not limited to the following embodiments.

In the present invention, "homology" means the degree of sequence similarity between two polypeptides or two polynucleotides, and is determined by comparing the two sequences aligned in the optimum state (sequence matching is in a maximum state) over the region of the amino acid sequence or base sequence to be compared. The numerical value (%) of homology is calculated by determining the number of sites having the same amino acids or bases in both aligned (amino acids or bases) sequences, and then by dividing the number of sites by the total number of amino acids or bases in the sequence region to be compared and multiplying the obtained numerical value by 100. Examples of algorithms for obtaining optimum alignment and homology include various algorithms (for example, BLAST algorithm, FASTA algorithm) generally available to those skilled in the art. The homology of amino acid sequence is determined using, for example, sequence analysis software such as BLASTP and FASTA. The homology of base sequence is determined using, for example, software such as BLASTN and FASTA.

The "host cell" into which the gene is introduced in the method of the present invention is not particularly limited, and examples thereof include prokaryotes such as *Escherichia coli* and *Bacillus subtilis*, and eukaryotes such as yeast and filamentous fungi. *Escherichia coli* is preferable as a host cell in the present invention.

In a case where the gene is introduced into the host cell, the gene may be introduced directly onto the host cell genomic DNA, but it is preferable to introduce a vector into which the gene is integrated into the host cell. All transgenes may be integrated into the same vector, or may be integrated into two or more vectors separately.

A vector (expression vector) expresses a transgene integrated therein. As a vector into which the transgene is integrated, a vector constructed from a plasmid or a phage that can autonomously replicate in the host cell for gene recombination is suitable. The vector preferably contains a replication initiation site suitable for the host cell to be introduced, a selectable marker, an expression control sequence such as a promoter, and a transcription termination signal (terminator sequence). Examples of the plasmid vector include a pET vector system, a pQE vector system, a pCold vector system, and the like in a case of being expressed in *Escherichia coli*, and include a pYES2 vector system, a pYEX vector system, and the like in a case of being expressed in yeast.

Examples of selectable markers include antibiotic resistance genes such as ampicillin resistance gene, kanamycin resistance gene, and streptomycin resistance gene.

The expression control sequence means a sequence that can control the expression of a gene composed of the DNA sequence in a host cell in a case of being appropriately linked to the DNA sequence, that is, induce and/or promote or suppress the transcription of the DNA sequence into RNA. The expression control sequence contains at least a promoter. The promoter may be a constitutive promoter or an inducible promoter.

The expression vector used in the present invention can be prepared by adding an appropriate restriction enzyme recognition site to the end of a desired gene by a conventional method.

As a method for transforming an expression vector into a host cell, a conventionally known method can be used, and examples thereof include a calcium chloride method, an electroporation method, and a heat shock method.

The culture conditions of the recombinant host cell are not particularly limited as long as the recombinant cell grows well, all the proteins of the target group are expressed, and the respective functions or enzymatic activities are exhibited. Specifically, the culture conditions may be appropriately selected in consideration of the nutritional and physiological properties of the host, and usually these include carrying out in a liquid culture.

The carbon source of the medium used for culturing the recombinant host cell is not particularly limited as long as the carbon source is a substance that can be used by the host cell, and examples thereof include sugar and glycerol. Examples of sugars include monosaccharides such as glucose, fructose, and galactose, and disaccharides such as sucrose, lactose, and maltose. Examples of the nitrogen source include ammonium sulfate and casamino acid. In addition, salts, specific amino acids, specific vitamins, and the like can be used as desired.

Examples of the medium for culturing *Escherichia coli* include LB medium, 2×YT medium, and M9 minimum medium. Examples of the medium for culturing yeast include SC medium, SD medium, and YPD medium.

The culture temperature can be appropriately changed as long as the host cell grows, the target enzyme is expressed, and the activity is exhibited. In a case of *Escherichia coli*, for example, culture conditions of a temperature of 25° C., 80 hours, and a pH of 7.0 can be used. In a case of yeast, for example, culture conditions of a temperature of 30° C., 60 hours, and a pH of 5.8 can be used.

The produced (R)-reticuline can be confirmed by any means well known to those of skill in the art. Specifically, the (R)-reticuline can be identified by supplying the reaction product and the target (R)-reticuline sample to an LC-MS and comparing the obtained spectra. The (R)-reticuline can also be confirmed by comparison by NMR analysis.

In the present specification, a case of "expressing" a specific gene means that the nucleic acid molecule constituting the gene is transcribed into at least an RNA molecule, and means that a nucleic acid molecule constituting the gene is transcribed into an RNA molecule and the RNA molecule is translated into a polypeptide in a case of a gene encoding a polypeptide.

The expression level of the gene can be confirmed by a method known in the technical fields such as Northern blotting, quantitative PCR, and the like.

In the present specification, a case of "expressing" a specific enzyme (protein) means a state where transcription from the nucleic acid molecule encoding a polypeptide of the enzyme into an RNA molecule and translation of the RNA molecule into a polypeptide are normally performed, and an active enzyme is produced and is present inside or outside the cell.

The expression level of the enzyme can be confirmed by detection and quantification using known methods such as Western blotting and ELISA. The expression level can also be confirmed by an assay for enzymatic activity.

Next, the "gene encoding STORR" (gene 3), "gene encoding CYP80Y2" (gene 1), "gene encoding oxidoreductase" (gene 2), "gene encoding 5-aminolevulinate synthase" (gene 4), and "gene encoding CPR" (gene 5), which are used in the present invention, will be described.

STORR is an enzyme derived from *Papaver somniferum* and is an epimerase that converts (S)-reticuline to (R)-reticuline. STORR is a fusion polypeptide including a domain of CYP80Y2 and a domain of oxidoreductase. In addition, SEQ ID NO: 9 is an amino acid sequence of STORR.

The "gene encoding STORR" used in the present invention is not limited to these, and may be, for example, the DNA described in any one of (a) to (c) below:
(a) DNA composed of the nucleotide sequence of SEQ ID NO: 1;
(b) DNA hybridizing with DNA composed of a nucleotide sequence complementary to the nucleotide sequence of SEQ ID NO: 1 under stringent conditions, and encoding a protein having the enzymatic activity (for example, epimerase activity to convert (S)-reticuline to (R)-reticuline) of STORR; and (c) DNA composed of a nucleotide sequence having 70% or more, preferably 80% or more, still more preferably 90% or more, and further preferably 95% or more homology to the nucleotide sequence of SEQ ID NO: 1, and encoding a protein having the enzymatic activity (for example, epimerase activity to convert (S)-reticuline to (R)-reticuline) of STORR.

In the present invention, as the "gene encoding STORR", DNA composed of (a) the nucleotide sequence of SEQ ID NO: 1 among the above-described (a) to (c) is preferably used.

CYP80Y2 is a P450 enzyme. CYP80Y2 has, for example, the activity of oxidizing (S)-reticuline to generate 1,2-dehydroreticlinium. In one embodiment of the present invention, in CYP80Y2, for example, the domain of CYP80Y2 contained in the above-described STORR may be separated from the domain of oxidoreductase. CYP80Y2 obtained by adding start methionine to the amino acid sequence shown in SEQ ID NO: 11 is an amino acid sequence of CYP80Y2 (in addition, the amino acid sequence shown in SEQ ID NO: 11 is obtained by further deleting the N-terminal hydrophobic region). SEQ ID NO: 10 is an amino acid sequence of the N-terminal hydrophobic region deleted in the present embodiment. In the SOSUI analysis, the amino acid sequence of the N-terminal hydrophobic region was PTSSVVALLLALVSILSSVVV, but in the present embodiment, the amino acid sequence was deleted from the start codon. By deleting the nucleotide sequence encoding the N-terminal hydrophobic region, the start codon sequence (atg) is inserted, the end codon sequence (taa) is introduced into the sequence immediately before the gene encoding oxidoreductase, and accordingly, a gene encoding CYP80Y2 is obtained by adding the start methionine to the amino acid sequence shown in SEQ ID NO: 11.

The "gene encoding CYP80Y2" used in the present invention is not limited to these, and may be, for example, the DNA described in any one of (a) to (c) below:

(a) DNA composed of the nucleotide sequence of SEQ ID NO: 2;

(b) DNA hybridizing with DNA composed of a nucleotide sequence complementary to the nucleotide sequence of SEQ ID NO: 2 under stringent conditions, and encoding a protein having the enzymatic activity (for example, activity to oxidize (S)-reticuline and generate 1,2-dehydroreticulineum) of CYP80Y2; and (c) DNA composed of a nucleotide sequence having 70% or more, preferably 80% or more, still more preferably 90% or more, and further preferably 95% or more homology to the nucleotide sequence of SEQ ID NO: 2, and encoding a protein having the enzymatic activity (for example, activity to oxidize (S)-reticuline and generate 1,2-dehydroreticulineum) of CYP80Y2.

In the present invention, as the "gene encoding CYP80Y2", DNA composed of (a) the nucleotide sequence of SEQ ID NO: 2 among the above-described (a) to (c) is preferably used.

The "gene encoding CYP80Y2" used in the present invention may be a gene in which the nucleotide sequence encoding the N-terminal hydrophobic region of the protein having the enzymatic activity of CYP80Y2 is deleted. By deleting (cutting) the base sequence of the N-terminal hydrophobic region, the transmembrane region is deleted.

The deletion of the base sequence of the N-terminal hydrophobic region of the "gene encoding CYP80Y2" may be performed by deleting the base sequence of the N-terminal hydrophobic region of the "gene encoding STORR". In other words, since the "gene encoding STORR" has a gene encoding CYP80Y2 on the N-terminal side and a gene encoding oxidoreductase on the C-terminal side, when the base sequence of the N-terminal hydrophobic region of the "gene encoding STORR" is deleted, the base sequence of the N-terminal hydrophobic region of the gene encoding CYP80Y2 is deleted.

In the present invention, the "N-terminal hydrophobic region" of the "gene encoding CYP80Y2" (or "gene encoding STORR") is a hydrophobic region which is present on the N-terminal side of the "gene encoding CYP80Y2" (or "gene encoding STORR"), for example, the base sequence shown in SEQ ID NO: 8.

Oxidoreductase referred to in the present invention is an oxidation-reduction enzyme having an enzymatic activity equivalent to that of the domain of oxidoreductase contained in the above-described STORR. In one embodiment of the present invention, in oxidoreductase, for example, the domain of oxidoreductase contained in the above-described STORR may be separated from the domain of CYP80Y2. SEQ ID NO: 12 is the amino acid sequence of oxidoreductase obtained in this manner.

The "gene encoding oxidoreductase" used in the present invention is not limited to these, and may be, for example, the DNA described in any one of (a) to (c) below:

(a) DNA composed of the nucleotide sequence of SEQ ID NO: 3;

(b) DNA hybridizing with DNA composed of a nucleotide sequence complementary to the nucleotide sequence of SEQ ID NO: 3 under stringent conditions, and encoding a protein having the enzymatic activity (for example, activity to reduce 1,2-dehydroreticulineium and generate (R)-reticuline) of oxidoreductase; and (c) DNA composed of a nucleotide sequence having 70% or more, preferably 80% or more, still more preferably 90% or more, and further preferably 95% or more homology to the nucleotide sequence of SEQ ID NO: 3, and encoding a protein having the enzymatic activity (for example, activity to reduce 1,2-dehydroreticulineium and generate (R)-reticuline) of oxidoreductase.

In the present invention, as the "gene encoding oxidoreductase", DNA composed of (a) the nucleotide sequence of SEQ ID NO: 3 among the above-described (a) to (c) is preferably used.

5-Aminolevulinate synthase 1 is an enzyme that synthesizes 5-aminolevulinic acid using succinyl-CoA and glycine as substrates and pyridoxal phosphate as a coenzyme.

The "gene encoding 5-aminolevulinate synthase 1" used in the present invention is not limited to these, and may be, for example, the DNA described in any one of (a) to (c) below:

(a) DNA composed of the nucleotide sequence of SEQ ID NO: 4;

(b) DNA hybridizing with DNA composed of a nucleotide sequence complementary to the nucleotide sequence of SEQ ID NO: 4 under stringent conditions, and encoding a protein having the enzymatic activity (for example, activity to synthesize 5-aminolevulinic acid using succinyl-CoA and glycine as substrates and pyridoxal phosphate as a coenzyme) of 5-aminolevulinate synthase 1; and (c) DNA composed of a nucleotide sequence having 70% or more, preferably 80% or more, still more preferably 90% or more, and further preferably 95% or more homology to the nucleotide sequence of SEQ ID NO: 4, and encoding a protein having the enzymatic activity (for example, activity to synthesize 5-aminolevulinic acid using succinyl-CoA and glycine as substrates and pyridoxal phosphate as a coenzyme) of 5-aminolevulinate synthase 1.

In the present invention, as the "gene encoding 5-aminolevulinate synthase 1", DNA composed of (a) the nucleotide sequence of SEQ ID NO: 4 among the above-described (a) to (c) is preferably used.

(a) A gene which is DNA composed of the nucleotide sequence of SEQ ID NO: 4 is called a HemA gene. The HemA gene is a gene encoding 5-aminolevulinate synthase 1 of *Rhodobacter sphaeroides*.

CPR (NADPH-cytochrome P450 reductase 2) is an enzyme for transferring electrons from NADP to cytochrome P450 in microsomes. CPR also plays a role in transferring electrons to heme oxygenase and cytochrome B5.

The "gene encoding CPR" used in the present invention is not limited to these, and may be, for example, the DNA described in any one of (a) to (c) below:
  (a) DNA composed of the nucleotide sequence of SEQ ID NO: 5;
  (b) DNA hybridizing with DNA composed of a nucleotide sequence complementary to DNA composed of a nucleotide sequence of SEQ ID NO: 5 under stringent conditions, and encoding a protein having the enzymatic activity (for example, activity to transfer electrons from NADP to cytochrome P450 in microsomes) of CPR.
  (c) DNA composed of a nucleotide sequence having 70% or more, preferably 80% or more, still more preferably 90% or more, and further preferably 95% or more homology to the nucleotide sequence of SEQ ID NO: 5, and encoding a protein having the enzymatic activity (for example, activity to transfer electrons from NADP to cytochrome P450 in microsomes) of CPR.

In the present invention, as the "gene encoding CPR", DNA composed of (a) the nucleotide sequence of SEQ ID NO: 5 among the above-described (a) to (c) is preferably used.

(a) A gene which is DNA composed of the nucleotide sequence of SEQ ID NO: 5 is called an ATR2 gene. The ATR2 gene is a gene encoding CPR of *Arabidopsis thaliana*.

The "stringent condition" refers to a condition in which only specific hybridization occurs and non-specific hybridization does not occur. Such conditions are generally approximately 6 M urea, 0.4% SDS, and 0.5×SSC. The DNA obtained by hybridization has preferably 70% or more, more preferably 80% or more, still more preferably 90% or more, and further preferably 95% or more homology with the DNA composed of the nucleotide sequence of each SEQ ID NO.

The gene can be acquired by PCR or hybridization techniques well known to those of skill in the art. Further, the above-described gene may be artificially synthesized using a DNA synthesizer or the like. Sequencing can be determined using a sequencer by a conventional method.
(Production Method of (R)-Reticuline)

The production method of (R)-reticuline of the present invention will be described.

FIG. 1 shows a biosynthetic pathway of (R)-reticuline reconstructed in a host cell in the present invention. Parentheses indicate the reaction in individual strains of each culture process. In the present invention, (R)-reticuline is produced by converting (S)-reticuline to (R)-reticuline. The abbreviations are: TYR, tyrosinase; DDC, DOPA decarboxylase; MAO, monoamine oxidase; 3,4-DHPAA, 3,4-dihydroxyphenylacetaldehyde; SalS, salutaridine synthase; SalR, salutaridine reductase; SalAT, salutaridinol acetyltransferase; and SPT (spontaneous).

Figure 2:
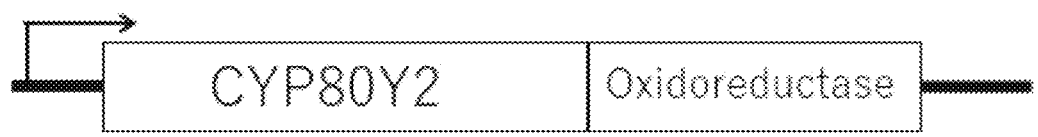
FIG. 2 is a schematic view showing a gene (FIG. 2(a)) encoding STORR in which a domain encoding CYP80Y2 and a domain encoding oxidoreductase are fused, and a gene (FIG. 2(b)) used in the present embodiment in which the domain encoding CYP80Y2 and the domain encoding oxidoreductase are separated.
Figure 2:

FIG. 2 is a schematic view showing the STORR gene (FIG. 2 (*a*)) and the STORR gene (FIG. 2 (*b*)) in which the domain of CYP80Y2 and the domain of oxidoreductase are separated.

The production method of (R)-reticuline of the present invention is to convert (S)-reticuline to (R)-reticuline, and (S)-reticuline is prepared in advance according to the conventional method. In the production method of (R)-reticuline of the present invention, for example, the following steps 1 to 4 are carried out in this order. A step (step 1) for dividing the gene encoding STORR (gene 3) into the gene encoding CYP80Y2 (gene 1) and the gene encoding oxidoreductase (gene 2). A step (step 2) for obtaining a recombinant host cell by inserting the gene encoding CYP80Y2 (gene 1) and the gene encoding oxidoreductase (gene 2) into a host cell. A step (step 3) for expressing a protein having the enzymatic activity of CYP80Y2 encoded by the gene 1 and a protein having the enzymatic activity of oxidoreductase encoded by the gene 2 in the recombinant host cell. A step (step 4) for producing (R)-reticuline from (S)-reticuline by a recombinant host cell.

The above-described step 1 can be omitted. In other words, in the production method of (R)-reticuline of the present invention, for example, the following steps 2 to 4 are carried out in this order. A step (step 2) for obtaining a recombinant host cell by inserting the gene encoding CYP80Y2 (gene 1) and the gene encoding oxidoreductase (gene 2) into a host cell. A step (step 3) for expressing a protein having the enzymatic activity of CYP80Y2 encoded by the gene 1 and a protein having the enzymatic activity of oxidoreductase encoded by the gene 2 in the recombinant host cell. A step (step 4) for producing (R)-reticuline from (S)-reticuline by a recombinant host cell.

The production method of (R)-reticuline in a case where the host cell is a prokaryote (for example, *Escherichia coli*), is as follows.

In the "gene encoding STORR" (gene 3), the nucleotide sequence encoding the N-terminal hydrophobic region is deleted in advance (step A). More specifically, among the "genes encoding STORR", the N-terminal hydrophobic region of the gene encoding CYP80Y2 is deleted (cut), and accordingly, the transmembrane region is deleted, the start codon sequence (atg) has been inserted, and the end codon sequence (taa) has been introduced into the sequence immediately before the gene encoding oxidoreductase.

The "gene encoding STORR" (gene 3) is divided into the "gene encoding CYP80Y2" (gene 1) and the "gene encoding oxidoreductase" (gene 2) (step B).

The "gene encoding CYP80Y2" (gene 1), the "gene encoding oxidoreductase" (gene 2), the "gene encoding 5-aminolevulinate synthase 1" (gene 4), and the "gene encoding CPR" (gene 5) are introduced into a host cell to obtain a recombinant host cell (step C). The introduction of these genes does not necessarily have to be performed in this order. The introduction may be performed at the same time, or the order may be changed.

In the recombinant host cell, the protein having the enzymatic activity of CYP80Y2 encoded by the gene 1, the protein having the enzymatic activity of oxidoreductase encoded by the gene 2, the protein having the enzymatic activity of 5-aminolevulinate synthase 1 encoded by the gene 4, and the protein having enzymatic activity of CPR encoded by the gene 5 are expressed (step D). (R)-reticuline is produced from (S)-reticuline by a recombinant host cell (step E).

The above-described step A and step B can be omitted. Further, instead of step A and step B, a step of deleting the nucleotide sequence encoding the N-terminal hydrophobic region of the protein having the enzymatic activity of CYP80Y2 from the "gene encoding CYP80Y2" (gene 1) (step X), may be carried out.

Example

An example made by the method of the present invention will be described. The following example is described as an example of the present invention and is not intended to limit the scope of the present invention.
(Material)

All synthetic genes are obtained from GenScript Inc. (S)-reticuline was prepared according to the method described in the prior art (for example, Nakagawa et al., 2011, Nat Commun).
(Construction of Expression Vector)

In order to reconstruct the pathway for synthesizing (R)-reticuline from (S)-reticuline, a plurality of expression vectors containing various genes were constructed.

In the present example, the gene encoding CYP80Y2 shown in SEQ ID NO: 2 and the gene encoding oxidoreductase shown in SEQ ID NO: 3, which were separated from the gene (UniProtKB: PODKI7) encoding STORR shown in SEQ ID NO: 1 in the sequence listing, were used. In addition, the HemA gene (UniProtKB: Q04512), which is a gene encoding 5-aminolevulinate synthase 1 shown in SEQ ID NO: 4, and the ATR2 gene (UniProtKB: Q9SUM3), which is a gene encoding CPR shown in SEQ ID NO: 5, were used. In each gene, codon is optimized for *Escherichia coli*.

Both genes were inserted into the NdeI-BamHI site of pET23a to realize the control by the T7 promoter. In a case of linking genes, first, by inserting the gene to be connected to the front of the NdeI-BamHI site of pET23a, and by inserting the gene to be connected to the back of the XhoI site positioned downstream of the NdeI-BamHI site, the expression vector was prepared. For example, in a case of inserting the gene encoding oxidoreductase after the gene encoding CYP80Y2, first, by inserting the gene encoding CYP80Y2 into the NdeI-BamHI site of pET23a, CYP80Y2/pET23a, which is an expression vector containing the gene encoding CYP80Y2 was prepared. Then, by using the primers of pr576 (SEQ ID NO: 6) and pr577 (SEQ ID NO: 7) shown in Table 1, the gene encoding oxidoreductase was amplified by PCR. Then, by inserting the gene encoding oxidoreductase by infusion into the XhoI site positioned downstream of the NdeI-BamHI site of CYP80Y2/pET23a, CYP80Y2-OxiRed/pET23a, which is an expression vector containing the gene encoding CYP80Y2 and the gene encoding oxidoreductase, was prepared.

TABLE 1

DNA sequence of used primers

| SEQ ID NO: | Primer name | Sequence |
|---|---|---|
| 6 | pr576 | GGTGGTGGTGCTCGAGTGCGGCCGCAAGCTTGTCG |
| 7 | pr577 | TGCGGCCGCACTCGACGATCCCGCGAAATTAATACGA |

In the present example, by the same method described above, as expression vectors, CYP80Y2Ncut-OxiRed/pET23a, ATR2/pCDF23, HemA/pCDF23, and ATR2-HemA/pCDF23 were constructed.

CYP80Y2Ncut-OxiRed/pET23a is an expression vector based on the pET23a plasmid containing the gene encoding CYP80Y2 in which the N-terminal hydrophobic region was deleted and the gene encoding oxidoreductase.

HemA/pCDF23 is an expression vector based on the pCDF23 plasmid containing the HemA gene, which is the gene encoding 5-aminolevulinate synthase 1.

ATR2/pCDF23 is an expression vector based on the pCDF23 plasmid containing the ATR2 gene, which is the gene encoding CPR.

ATR2-HemA/pCDF23 is an expression vector based on the pCDF23 plasmid containing the HemA gene, which is the gene encoding 5-aminolevulinate synthase 1, and the ATR2 gene, which is the gene encoding CPR.

Next, various *Escherichia coli* strains, AN2534 strain, AN4415 strain, AN4340 strain, and AN4341 strain were prepared. The AN2534 strain is a strain in which CYP80Y2Ncut-OxiRed/pET23a is introduced into BL21DE3 strain, which is an *Escherichia coli* competent cell. The AN4415 strain is a strain in which pCDF23, which is the empty vector, is introduced into the AN2534 strain. The AN4340 strain is a strain in which ATR2/pCDF23 is introduced into the AN2534 strain. The AN4341 strain is a strain in which HemA/pCDF23 is introduced into the AN2534 strain. AN2051 is a strain in which ATR2-HemA/pCDF23 is introduced into the AN2534 strain.

Each *Escherichia coli* strain was inoculated into LB medium (Difco) containing 50 mg/L ampicillin and 100 mg/L spectinomycin, and was cultured at 37° C. for 12 hours with shaking. Then, the culture medium was added to TB medium (per 1 L: 12 g tryptone (Difco), 24 g yeast extract (Diffco), 9.4 g $K_2HPO_4$, 2.2 g $K_2HPO_4$, and 4 ml glycerol) containing 50 mg/L ampicillin and 100 mg/L spectinomycin in a volume of 1/100. After culturing at 25° C. for 12 hours, IPTG was added such that a final concentration is 1 mM, and the cells were further cultured with shaking at 25° C. for 12 hours. A culture supernatant (for example, prepared by the method described in Nakagawa et al., 2011, Nat Commun) containing 320 μM S-reticuline produced using *Escherichia coli* was mixed in an equivalent amount, and further infiltrated and cultured at 25° C. for 12 hours. The culture supernatant was collected and the chirality of reticuline was observed by the methods described in Non-Patent Literature 1 and 2. The results are shown in Table 2.

TABLE 2

| | Reticuline production amount (ion count × $10^7$) | | |
|---|---|---|---|
| | Strain | (S)-reticuline | (R)-reticuline |
| none | AN4415 | 4.97 | 0 |
| ATR2 | AN4340 | 4.93 | 0 |
| HemA | AN4341 | 5.03 | 0 |
| ATR2 + HemA | AN2051 | 0 | 4.72 |

As shown in Table 2, only AN2051 strain introduced with the gene encoding CYP80Y2 in which the N-terminal hydrophobic region was deleted, the gene encoding oxidoreductase, the HemA gene which is the gene encoding 5-aminolevulinate synthase 1, and the ATR2 gene which is the gene encoding CPR, can produce (R)-reticuline.

Figure 3:
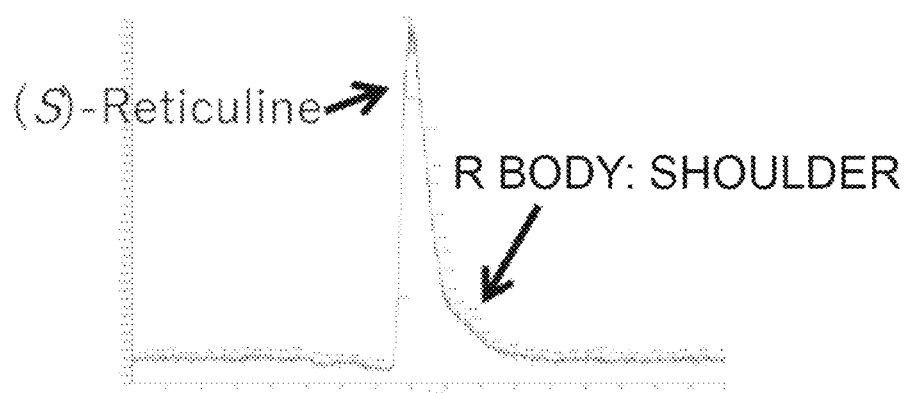
FIG. 3 is an LC-MS analysis result showing the generation of (R)-reticuline in the present embodiment.
Figure 3:
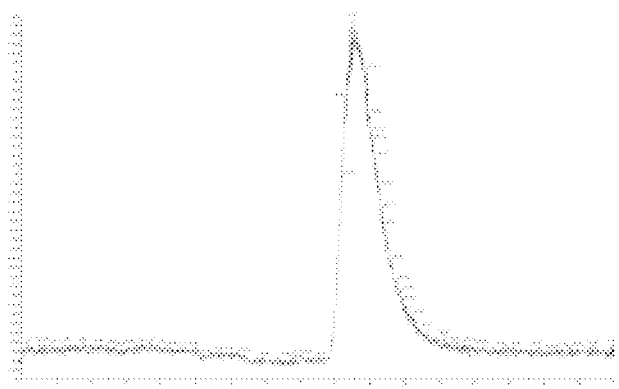
Figure 3:
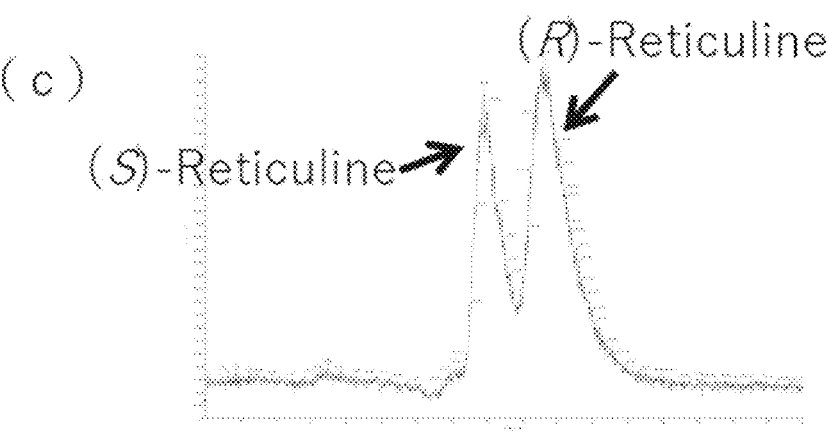

FIG. 3 is an LC-MS analysis result showing the generation of (R)-reticuline in the present embodiment. FIG. 3(*a*)

shows the result of introducing the gene encoding STORR shown in SEQ ID NO: 1 into a host cell in full length (that is, without dividing the gene encoding CYP80Y2 and the gene encoding oxidoreductase). FIG. 3(b) shows the result of introducing the gene encoding STORR shown in SEQ ID NO: 1 into a host cell by dividing the gene encoding CYP80Y2 and the gene encoding oxidoreductase. FIG. 3(c) is a result of stacking these samples, and is a diagram showing that the peak of FIG. 3(a) and the peak of FIG. 3(b) do not overlap.

As shown in FIG. 3(a), it is shown that even when the gene encoding STORR was introduced into the host cell in full length, (R)-reticuline could not be generated. Then, as shown in FIG. 3(b), it is shown that (R)-reticuline can be obtained by dividing the gene encoding STORR into the gene encoding CYP80Y2 and the gene encoding oxidoreductase and introducing the divided genes into the host cell. In other words, when the two domains of STORR were expressed separately, strong activity was obtained, and a sufficient amount (up to 100 μM) of (R)-reticuline could be produced.

In addition, from the results in Table 2 and FIG. 3, it is shown that (R)-reticuline with extremely high conversion efficiency can be obtained by introducing, into the host cell, the gene encoding CYP80Y2 in which the N-terminal hydrophobic region was deleted, the gene encoding oxidoreductase, the HemA gene which is the gene encoding 5-aminolevulinate synthase 1, and the ATR2 gene which is the gene encoding CPR.

In the present example, a prokaryote was used as the host cell, but the present invention is not limited thereto. In other words, it is also possible to use a eukaryote as a host cell. Since the P450 enzyme and the salutaridine synthase (SalS) are functionally expressed in a eukaryote, it is possible to more easily produce (R)-reticuline from (S)-reticuline. For example, it is considered that, when the gene encoding CYP80Y2 and the gene encoding oxidoreductase are introduced into a eukaryote (yeast), (R)-reticuline is produced from (S)-reticuline. Naturally, it is considered that, even when the gene encoding ATR2 and/or the gene encoding HemA are introduced into a eukaryote (yeast) in addition to the gene encoding CYP80Y2 and the gene encoding oxidoreductase, (R)-reticuline is produced from (S)-reticuline. As described above, the present invention is applicable to the extent that the present invention does not deviate from the gist thereof.

The invention claimed is:

1. A production method of (R)-reticuline comprising:
   obtaining a recombinant host cell by inserting, into a host cell,
   a gene 1 that comprises a nucleotide sequence having at least 70% homology to the nucleotide sequence of SEQ ID NO: 2, and
   a gene 2 that comprises a nucleotide sequence having at least 70% homology to the nucleotide sequence of SEQ ID NO: 3 and encodes a protein having an enzymatic activity of oxidoreductase;
   expressing, in the recombinant host cell, a protein encoded by the gene 1 and the protein having the enzymatic activity of oxidoreductase; and producing (R)-reticuline from (S)-reticuline by using the recombinant host cell,
wherein the host cell is a prokaryote.

2. The production method of (R)-reticuline according to claim 1, further comprising at least one of:
deleting the nucleotide sequence encoding an N-terminal hydrophobic region of the protein encoded by the gene 1,
expressing a protein having an enzymatic activity of 5-aminolevulinate synthase 1 by introducing, into the host cell, a gene 4 that comprises a nucleotide sequence having at least 70% homology to the nucleotide sequence of SEQ ID NO: 4 and encodes the protein having an enzymatic activity of 5-aminolevulinate synthase 1, and
expressing a protein having an enzymatic activity of CPR by introducing, into the host cell, a gene 5 that comprises a nucleotide sequence having at least 70% homology to the nucleotide sequence of SEQ ID NO: 5 and encodes the protein having the enzymatic activity of CPR.

3. The production method of (R)-reticuline according to claim 1, further comprising:
deleting the nucleotide sequence encoding an N-terminal hydrophobic region of the protein encoded by the gene 1;
expressing a protein having an enzymatic activity of 5-aminolevulinate synthase 1 by introducing, into the host cell, a gene 4 that comprises a nucleotide sequence having at least 70% homology to the nucleotide sequence of SEQ ID NO: 4 and encodes the protein having an enzymatic activity of 5-aminolevulinate synthase 1; and
expressing the protein having an enzymatic activity of CPR by introducing, into the host cell, a gene 5 that comprises a nucleotide sequence having at least 70% homology to the nucleotide sequence of SEQ ID NO: 5 and encodes the protein having the enzymatic activity of CPR.

4. The production method of (R)-reticuline according to claim 3, wherein the prokaryote is *Escherichia coli*.

5. The production method of (R)-reticuline according to claim 1, further comprising
dividing a gene 3 that comprises a nucleotide sequence having at least 70% homology to the nucleotide sequence of SEQ ID NO: 1 and encodes a protein having an enzymatic activity of STORR into the gene 1 and the gene 2.

6. The production method of (R)-reticuline according to claim 5, further comprising at least one of:
deleting the nucleotide sequence encoding an N-terminal hydrophobic region of the protein encoded by the gene 1,
expressing a protein having an enzymatic activity of 5-aminolevulinate synthase 1 by introducing, into the host cell, a gene 4 that comprises a nucleotide sequence having at least 70% homology to the nucleotide sequence of SEQ ID NO: 4 and encodes the protein having an enzymatic activity of 5-aminolevulinate synthase 1, and
expressing a protein having an enzymatic activity of CPR by introducing, into the host cell, a gene 5 that comprises a nucleotide sequence having at least 70% homology to the nucleotide sequence of SEQ ID NO: 5 and encodes the protein having the enzymatic activity of CPR.

7. The production method of (R)-reticuline according to claim 5, further comprising:
deleting the nucleotide sequence encoding an N-terminal hydrophobic region of the protein encoded by the gene 1;
expressing a protein having an enzymatic activity of 5-aminolevulinate synthase 1 by introducing, into the host cell, a gene 4 that comprises a nucleotide sequence having at least 70% homology to the nucleotide sequence of SEQ ID NO: 4 and encodes the protein having an enzymatic activity of 5-aminolevulinate synthase 1; and
expressing the protein having an enzymatic activity of CPR by introducing, into the host cell, a gene 5 that comprises a nucleotide sequence having at least 70% homology to the nucleotide sequence of SEQ ID NO: 5 and encodes the protein having the enzymatic activity of CPR.

8. The production method of (R)-reticuline according to claim 1, wherein the protein encoded by the gene 1 has an enzymatic activity of a protein encoded by SEQ ID NO: 2.

9. The production method of (R)-reticuline according to claim 1, wherein the protein encoded by the gene 1 has an enzymatic activity of a protein encoded by CYP82Y2.

10. The production method of (R)-reticuline according to claim 1, wherein the gene 1 comprises a nucleotide sequence having at least 90% homology to the nucleotide sequence of SEQ ID NO: 2.

* * * * *

SEQUENCE LISTING

<160> NUMBER OF SEQ ID NOS: 12

<210> SEQ ID NO 1
<211> LENGTH: 2706
<212> TYPE: DNA
<213> ORGANISM: Papaver somniferum

<400> SEQUENCE: 1

```
atggaactgc aatacatctc ctactttcaa ccgacctcgt ctgtggtggc actgctgctg     60
gctctggtgt ctatcctgtc tagcgtcgtg gttctgcgta aaacctttct gaacaattat    120
agctctagtc cggcatcctc aaccaaaacg gctgtgctgt cccatcagcg ccagcaatca    180
tgcgccctgc cgatttcggg tctgctgcat atcttcatga ataaaaacgg cctgatccac    240
gttaccctgg gtaatatggc agataaatac ggcccgattt ttagcttccc gaccggttca    300
caccgtacgc tggtcgtgtc gagctgggaa atggtgaaag aatgttttac cggcaacaat    360
gacacggcgt tctctaaccg cccgattccg ctggcgttta aaaccatctt ctatgcctgc    420
ggcggtattg atagttacgg tctgtctagt gttccgtatg gcaaatactg gcgtgaactg    480
cgcaaagtct gtgtgcataa tctgctgagc aaccagcaac tgctgaaatt tcgtcacctg    540
attatctcgc aggtggacac cagcttcaat aaactgtatg aactgtgcaa aaactctgaa    600
gataatcatg gtaactacac caccaccacc accaccgccg cgggtatggt tcgtattgat    660
gactggctgg cggaactgag ttttaatgtg attggccgca tcgtttgtgg tttccagtct    720
ggcccgaaaa ccggtgcccc gagtcgtgtg gaacaattca agaagcaat caacgaagct    780 tcctatttca tgtctacgag tccggtctca gacaacgtgc cgatgctggg ttggattgat    840
cagctgaccg gcctgacgcg caatatgaaa cattgcggta aaaaactgga cctggttgtc    900
gaatcgatta tcaacgatca ccgtcagaaa cgtcgcttta gccgcaccaa aggcggtgac    960
gaaaaagatg acgaacaaga tgacttcatt gatatctgtc tgagtatcat ggaacagccg   1020
caactgccgg gcaacaataa cccgagccag attccgatca aatctattgt gctggacatg   1080
atcggcggtg gcaccgatac cacgaaactg accacgattt ggacgctgtc cctgctgctg   1140
aataacccgc atgtcctgga caaagcgaaa caggaagtgg atgcccactt tcgtaccaaa   1200
```

```
cgtcgctcaa cgaatgacgc agctgcggcc gtggttgatt tcgatgacat tcgcaacctg   1260
gtgtacatcc aagcaatcat caaagaatca atgcgtctgt atccggctag cccggttgtg   1320
gaacgtctga gcggtgaaga ttgcgttgtc ggtggctttc acgttccggc aggcacccgt   1380
ctgtgggcta atgtctggaa aatgcagcgc gatccgaaag tgtgggatga cccgctggtt   1440
tttcgtccgg atcgcttcct gtctgacgaa cagaaaatgg ttgatgtccg tggtcaaaac   1500
tatgaactgc tgccgtttgg tgccggtcgt cgcgtttgcc cgggcgtctc cttctcactg   1560
gatctgatgc agctggtgct gacccgcctg attctggaat ttgaaatgaa atcgccgagc   1620
ggtaaagtgg acatgaccgc cacgccgggc ctgatgagct acaaagttat tccgctggat   1680
atcctgctga cgcatcgtcg catcaaaccg tgtgttcagt ccgcagcttc agaacgtgat   1740
atggaatcct caggtgtgcc ggttattacc ctgggttccg gcaaagtcat gccggtgctg   1800
ggtatgggca cgtttgaaaa agtgggtaaa ggctcagaac gtgaacgcct ggcgattctg   1860
aaagccatcg aagttggcta tcgttacttc gataccgcgg ccgcgtatga acggaagaa    1920 gtcctgggtg aagccatcgc agaagctctg cagctgggcc tggtgaaaag ccgcgatgaa   1980
ctgtttattt cgagcatgct gtggtgcacc gatgcccatg cggaccgtgt tctgctggca   2040
ctgcaaaatt cgctgcgcaa cctgaaactg aatatgtcg atctgtacat gctgccgttc    2100
ccggccagcc tgaaaccggg taaaattacc atggatatcc cggaagaaga catttgccgt   2160
atggattatc gctctgtgtg ggctgcgatg aagaatgtc agaatctggg ctttaccaaa    2220
agtatcggtg tttcgaactt cagctgcaaa aaactgcagg aactgatggc aacggctaat   2280
attccgccgg cggttaacca agtcgaaatg tcgccggcct ttcagcagaa aaaactgcgc   2340
gaatactgta cgcaaataa cattctggtc tctgctatca gtgtgctggg tagcaatggc    2400
accccgtggg gcagtaacgc ggttctgggt tccgaagtcc tgaagaaaat tgcgatggcc   2460
aagggtaaat ctgtggccca agttagtatg cgttgggtgt atgaacaagg cgcatccctg   2520
gtggttaaat cttttagtga agaacgtctg cgcgaaaatc tgaacatctt cgactgggaa   2580
ctgaccaaag aagatcatga aaaaattggc gaaatcccgc agtgtcgcat tctgagcgcg   2640
tactttctgg ttagcccgaa tggcccgttc aaatctcaag aagaactgtg ggacgacgaa   2700
gcctga                                                              2706
```

<210> SEQ ID NO 2
<211> LENGTH: 1650
<212> TYPE: DNA
<213> ORGANISM: Papaver somniferum

<400> SEQUENCE: 2

```
atgcgtaaaa cctttctgaa caattatagc tctagtccgg catcctcaac caaaacggct     60
gtgctgtccc atcagcgcca gcaatcatgc gccctgccga tttcgggtct gctgcatatc    120
ttcatgaata aaaacggcct gatccacgtt accctgggta atatggcaga taaatacggc    180
ccgattttta gcttcccgac cggttcacac cgtacgctgg tcgtgtcgag ctgggaaatg    240
gtgaaagaat gttttaccgg caacaatgac acggcgttct ctaaccgccc gattccgctg    300
gcgtttaaaa ccatcttcta tgcctgcggc ggtattgata gttacggtct gtctagtgtt    360
ccgtatggca aatactggcg tgaactgcgc aaagtctgtg tgcataatct gctgagcaac    420
cagcaactgc tgaaatttcg tcacctgatt atctcgcagg tggacaccag cttcaataaa    480
ctgtatgaac tgtgcaaaaa ctctgaagat aatcatggta actacaccac caccaccacc    540
```

```
accgccgcgg gtatggttcg tattgatgac tggctggcgg aactgagttt taatgtgatt      600
ggccgcatcg tttgtggttt ccagtctggc ccgaaaaccg gtgccccgag tcgtgtggaa      660
caattcaaag aagcaatcaa cgaagcttcc tatttcatgt ctacgagtcc ggtctcagac      720
aacgtgccga tgctgggttg gattgatcag ctgaccggcc tgacgcgcaa tatgaaacat      780
tgcggtaaaa aactggacct ggttgtcgaa tcgattatca acgatcaccg tcagaaacgt      840
cgctttagcc gcaccaaagg cggtgacgaa aaagatgacg aacaagatga cttcattgat      900
atctgtctga gtatcatgga acagccgcaa ctgccgggca caataacccc gagccagatt      960
ccgatcaaat ctattgtgct ggacatgatc ggcggtggca ccgataccac gaaactgacc     1020
acgatttgga cgctgtccct gctgctgaat aacccgcatg tcctggacaa agcgaaacag     1080
gaagtggatg cccactttcg taccaaacgt cgctcaacga atgacgcagc tgcggccgtg     1140
gttgatttcg atgacattcg caacctggtg tacatccaag caatcatcaa agaatcaatg     1200
cgtctgtatc cggctagccc ggttgtgaaa cgtctgagcg gtgaagattg cgttgtcggt     1260
ggctttcacg ttccggcagg cacccgtctg tgggctaatg tctggaaaat gcagcgcgat     1320
ccgaaagtgt gggatgaccc gctggttttt cgtccggatc gcttcctgtc tgacgaacag     1380
aaaatggtta tgtccgtgg tcaaaactat gaactgctgc cgtttggtgc cggtcgtcgc     1440
gtttgcccgg gcgtctcctt ctcactggat ctgatgcagc tggtgctgac ccgcctgatt     1500
ctggaatttg aaatgaaatc gccgagcggt aaagtggaca tgaccgccac gccgggcctg     1560
atgagctaca agttattcc gctggatatc ctgctgacgc atcgtcgcat caaaccgtgt     1620
gttcagtccg cagcttcaga acgtgattaa                                       1650

<210> SEQ ID NO 3
<211> LENGTH: 966
<212> TYPE: DNA
<213> ORGANISM: Papaver somniferum

<400> SEQUENCE: 3
atggaatcct caggtgtgcc ggttattacc ctgggttccg gcaaagtcat gccggtgctg       60
ggtatgggca cgtttgaaaa agtgggtaaa ggctcagaac gtgaacgcct ggcgattctg      120
aaagccatcg aagttggcta tcgttacttc gataccgcgg ccgcgtatga acggaagaa      180 gtcctgggtg aagccatcgc agaagctctg cagctgggcc tggtgaaaag ccgcgatgaa      240
ctgtttattt cgagcatgct gtggtgcacc gatgcccatg cggaccgtgt tctgctggca      300
ctgcaaaatt cgctgcgcaa cctgaaactg gaatatgtcg atctgtacat gctgccgttc      360
ccggccagcc tgaaaccggg taaaattacc atggatatcc cggaagaaga catttgccgt      420
atggattatc gctctgtgtg ggctgcgatg aagaatgtc agaatctggg ctttaccaaa      480
agtatcggtg tttcgaactt cagctgcaaa aaactgcagg aactgatggc aacggctaat      540
attccgccgg cggttaacca agtcgaaatg tcgccggcct ttcagcagaa aaaactgcgc      600
gaatactgta acgcaaataa cattctggtc tctgctatca gtgtgctggg tagcaatggc      660 acccgtggg gcagtaacgc ggttctgggt tccgaagtcc tgaagaaaat tgcgatggcc      720
aagggtaaat ctgtggccca agttagtatg cgttgggtgt atgaacaagg cgcatccctg      780
gtggttaaat ctttagtga agaacgtctg cgcgaaaatc tgaacatctt cgactgggaa      840
ctgaccaaag aagatcatga aaaaattggg gaaatcccgc agtgtcgcat tctgagcgcg      900
tactttctgg ttagcccgaa tggcccgttc aaatctcaag aagaactgtg ggacgacgaa      960
gcctga                                                                966
```

<210> SEQ ID NO 4
<211> LENGTH: 2136
<212> TYPE: DNA
<213> ORGANISM: Arabidopsis thaliana

<400> SEQUENCE: 4

| | | |
|---|---|---|
| atgagcagca gcagtagctc ttccaccagc atgattgacc tgatggcagc cattatcaaa | 60 |
| ggcgaaccgg ttattgttag cgacccggcg aacgcatcag cttatgaatc ggtggcggcc | 120 |
| gaactgagct ctatgctgat tgaaaatcgt cagtttgcga tgattgtcac cacgagtatc | 180 |
| gccgtgctga ttggctgcat cgttatgctg gtctggcgtc gcagcggctc tggtaactcc | 240 |
| aaacgcgttg aaccgctgaa accgctggtc attaagccgc gtgaagaaga aatcgatgac | 300 |
| ggccgcaaaa aggttacgat tttctttggt acccagacgg gcaccgcgga ggtttcgcg | 360 |
| aaagccctgg gtgaagaagc aaaggctcgt tatgaaaaaa cccgctttaa gatcgttgat | 420 |
| ctggatgact atgcagctga tgacgatgaa tacgaagaaa aactgaaaaa ggaagatgtc | 480 |
| gcgttttct ttctggccac gtatggcgat ggtgaaccga ccgacaatgc ggcccgtttc | 540 |
| tacaaatggt ttaccgaagg caacgatcgc ggtgaatggc tgaaaaatct gaagtatggc | 600 |
| gtgttcggcc tgggtaaccg tcagtacgaa cattttaata aagtggcaaa ggtggttgac | 660 |
| gatattctgg ttgaacaggg tgcgcaacgc ctggttcagg tcggcctggg tgacgatgac | 720 |
| caatgtattg aagatgactt taccgcctgg cgtgaagccc gtggccgga actggacacg | 780 |
| atcctgcgcg aagaaggtga taccgccgtg gcaaccccgt ataccgcagc tgtcctggaa | 840 |
| taccgtgtga gcattcatga ttctgaagac gcaaaattca cgacatcaa tatggctaac | 900 |
| ggcaatggtt atacggtttt tgatgcgcag cacccgtaca agcgaacgt ggccgttaag | 960 |
| cgtgaactgc atacccccgga atcagaccgc tcgtgcattc acctggaatt tgatatcgcc | 1020 |
| ggctcaggtc tgacgtatga aaccggcgat catgtcggcg tgctgtgcga caatctgtcg | 1080 |
| gaaaccgtgg atgaagccct cgcctgctg gatatgtcac cggacacgta cttctcgctg | 1140 |
| cacgccgaaa agaagatgg caccccgatt agttccagcc tgccgccgcc gtttccgccg | 1200 |
| tgcaacctgc gtacggcact gacccgctat gcttgtctgc tgtcgagccc gaaaaagagc | 1260 |
| gcactggtgg ctctggccgc acatgcatct gatccgaccg aagctgaacg tctgaaacac | 1320 |
| ctggcgtcac cggccggtaa agatgaatac tcgaagtggg tcgtgaaaag ccagcgtagc | 1380 |
| ctgctggaag ttatggcgga attcccgagc gccaaaccgc cgctgggcgt tttctttgcg | 1440 |
| ggtgttgctc cgcgtctgca accgcgtttt tatagcattt ctagttcccc gaaaattgcg | 1500 |
| gaaacgcgta tccatgtgac ctgcgccctg gtttacgaaa aaatgccgac gggccgcatc | 1560 |
| cacaagggtg tctgcagtac ctggatgaaa acgccgtgc cgtatgaaaa gtccgaaaat | 1620 |
| tgttcatcgg caccgatttt cgtccgtcag agcaatttta aactgccgag tgattccaag | 1680 |
| gtgccgatta tcatgattgg tccgggtacc ggtctggcac cgttccgtgg ctttctgcaa | 1740 |
| gaacgcctgg ctctggtgga agcggcgtt gaactgggtc cgtctgtgct gttctttggt | 1800 |
| tgccgtaacc gtcgcatgga tttcatttat gaagaagaac tgcagcgttt tgttgaatct | 1860 |
| ggcgcactgg ctgaactgag tgtcgcgttt tcccgcgaag gtccgaccaa gaatacgtt | 1920 |
| cagcataaaa tgatggataa ggcgagtgac atttggaata tgatctccca aggcgcctat | 1980 |
| ctgtatgttt gcggcgacgc aaagggtatg gctcgtgatg ttcatcgcag cctgcacacg | 2040 |
| atcgcgcagg aacaaggtag tatggattcc accaaagcgg aaggctttgt gaaaaatctg | 2100 |

```
caaacgagtg gtcgctatct gcgtgatgtc tggtga                              2136

<210> SEQ ID NO 5
<211> LENGTH: 1224
<212> TYPE: DNA
<213> ORGANISM: Rhodobacter capsulatus

<400> SEQUENCE: 5
atggactaca acttagcgct ggataccgcc ctcaatcgcc tgcataccga gggtcgttat      60
cgcacgttca tcgatatcga acgccggaaa ggagcgtttc cgaaagcgat gtggcgtaaa     120
cccgatggta gcgagaagga gattactgtc tggtgtggta atgactatct gggcatgggc     180
caacatccgg tagtcctggg cgcgatgcat gaagcgctgg atagcactgg cgcggggagt     240
ggtggtacgc gcaacattag cggcacaacg ctgtaccaca agcgcctgga agcagaactt     300
gccgatcttc atggcaaaga agcagcgctt gtgttttcgt ctgcgtatat cgcgaacgat     360
gcgactcttt ccacactccc gcagttgatc ccgggcttgg tgattgtgtc ggacaaactg     420
aaccacgcaa gcatgattga aggaattcgc cgtagtggca ccgaaaagca cattttcaag     480
cataacgatc tggatgactt acgccgcatc ctgacctcca tcggcaaaga tcgtccgatt     540
ctggtggcct ttgaaagtgt gtactcgatg gatggcgact ttggtcgtat tgaggagatt     600
tgcgacattg ccgacgaatt cggggctctc aaatacatcg acgaggtgca tgccgtaggt     660
atgtatggtc cacgtggcgg tggtgttgcg gaacgggatg ggctcatgga ccgcattgat     720
atcatcaatg gcacgctggg aaaagcgtat ggtgtctttg cgggtacat tgctgccagc     780 tcgaaaatgt gcgatgcagt gcgtagctat gctccgggct tcatcttctc aacctctctg     840
ccacctgttg tggctgccgg agcagctgct tctgttcgcc atctgaaagg tgatgttgaa     900
ctgcgtgaga acatcagac gcaagcacgc atttttgaaaa tgcgcctgaa aggcttaggc     960
ctgccgatta tcgatcacgg ctcacacatt gttccggtcc atgtgggtga cccggtccac    1020
tgcaaaatga tcagtgacat gttgctggaa cactttggga tctatgtaca gcccattaac    1080
ttccctaccg tacctcgtgg gaccgaacgc ttacgcttta ccccatcacc ggtgcacgat    1140
tccggtatga ttgatcatct ggtgaaagca atggatgtct tatggcagca ttgtgccctg    1200
aatcgtgcgg aagttgttgc ctaa                                          1224

<210> SEQ ID NO 6
<211> LENGTH: 35
<212> TYPE: DNA
<213> ORGANISM: Artificial Sequence
<220> FEATURE:
<223> OTHER INFORMATION: synthetic primer (pr576)

<400> SEQUENCE: 6
ggtggtggtg ctcgagtgcg gccgcaagct tgtcg                                35

<210> SEQ ID NO 7
<211> LENGTH: 37
<212> TYPE: DNA
<213> ORGANISM: Artificial Sequence
<220> FEATURE:
<223> OTHER INFORMATION: synthetic primer (pr577)

<400> SEQUENCE: 7
tgcggccgca ctcgacgatc ccgcgaaatt aatacga                              37

<210> SEQ ID NO 8
<211> LENGTH: 96
```

<212> TYPE: DNA
<213> ORGANISM: Papaver somniferum

<400> SEQUENCE: 8

```
atggaactgc aatacatctc ctactttcaa ccgacctcgt ctgtggtggc actgctgctg    60
gctctggtgt ctatcctgtc tagcgtcgtg gttctg                              96
```

<210> SEQ ID NO 9
<211> LENGTH: 901
<212> TYPE: PRT
<213> ORGANISM: Papaver somniferum

<400> SEQUENCE: 9

```
Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
    210                 215                 220

Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
            260                 265                 270

Val Pro Met Leu Gly Trp Ile Asp Gln Leu Thr Gly Leu Thr Arg Asn
        275                 280                 285

Met Lys His Cys Gly Lys Lys Leu Asp Leu Val Val Glu Ser Ile Ile
    290                 295                 300

Asn Asp His Arg Gln Lys Arg Phe Ser Arg Thr Lys Gly Gly Asp
305                 310                 315                 320

Glu Lys Asp Asp Glu Gln Asp Asp Phe Ile Asp Ile Cys Leu Ser Ile
                325                 330                 335
```

```
Met Glu Gln Pro Gln Leu Pro Gly Asn Asn Pro Ser Gln Ile Pro
            340                 345                 350

Ile Lys Ser Ile Val Leu Asp Met Ile Gly Gly Thr Asp Thr Thr
            355                 360                 365

Lys Leu Thr Thr Ile Trp Thr Leu Ser Leu Leu Asn Asn Pro His
            370                 375                 380

Val Leu Asp Lys Ala Lys Gln Glu Val Asp Ala His Phe Arg Thr Lys
385                 390                 395                 400

Arg Arg Ser Thr Asn Asp Ala Ala Ala Val Val Asp Phe Asp Asp
            405                 410                 415

Ile Arg Asn Leu Val Tyr Ile Gln Ala Ile Ile Lys Glu Ser Met Arg
            420                 425                 430

Leu Tyr Pro Ala Ser Pro Val Val Glu Arg Leu Ser Gly Glu Asp Cys
            435                 440                 445

Val Val Gly Gly Phe His Val Pro Ala Gly Thr Arg Leu Trp Ala Asn
            450                 455                 460

Val Trp Lys Met Gln Arg Asp Pro Lys Val Trp Asp Asp Pro Leu Val
465                 470                 475                 480

Phe Arg Pro Asp Arg Phe Leu Ser Asp Glu Gln Lys Met Val Asp Val
                    485                 490                 495

Arg Gly Gln Asn Tyr Glu Leu Leu Pro Phe Gly Ala Gly Arg Arg Val
            500                 505                 510

Cys Pro Gly Val Ser Phe Ser Leu Asp Leu Met Gln Leu Val Leu Thr
            515                 520                 525

Arg Leu Ile Leu Glu Phe Glu Met Lys Ser Pro Ser Gly Lys Val Asp
            530                 535                 540

Met Thr Ala Thr Pro Gly Leu Met Ser Tyr Lys Val Ile Pro Leu Asp
545                 550                 555                 560

Ile Leu Leu Thr His Arg Arg Ile Lys Pro Cys Val Gln Ser Ala Ala
                    565                 570                 575

Ser Glu Arg Asp Met Glu Ser Ser Gly Val Pro Val Ile Thr Leu Gly
            580                 585                 590

Ser Gly Lys Val Met Pro Val Leu Gly Met Gly Thr Phe Glu Lys Val
            595                 600                 605

Gly Lys Gly Ser Glu Arg Glu Arg Leu Ala Ile Leu Lys Ala Ile Glu
            610                 615                 620

Val Gly Tyr Arg Tyr Phe Asp Thr Ala Ala Tyr Glu Thr Glu Glu
625                 630                 635                 640

Val Leu Gly Glu Ala Ile Ala Glu Ala Leu Gln Leu Gly Leu Val Lys
                    645                 650                 655

Ser Arg Asp Glu Leu Phe Ile Ser Ser Met Leu Trp Cys Thr Asp Ala
            660                 665                 670

His Ala Asp Arg Val Leu Leu Ala Leu Gln Asn Ser Leu Arg Asn Leu
            675                 680                 685

Lys Leu Glu Tyr Val Asp Leu Tyr Met Leu Pro Phe Pro Ala Ser Leu
            690                 695                 700

Lys Pro Gly Lys Ile Thr Met Asp Ile Pro Glu Glu Asp Ile Cys Arg
705                 710                 715                 720

Met Asp Tyr Arg Ser Val Trp Ala Ala Met Glu Glu Cys Gln Asn Leu
                    725                 730                 735

Gly Phe Thr Lys Ser Ile Gly Val Ser Asn Phe Ser Cys Lys Lys Leu
            740                 745                 750
```

```
Gln Glu Leu Met Ala Thr Ala Asn Ile Pro Pro Ala Val Asn Gln Val
            755                 760                 765

Glu Met Ser Pro Ala Phe Gln Gln Lys Lys Leu Arg Glu Tyr Cys Asn
        770                 775                 780

Ala Asn Asn Ile Leu Val Ser Ala Ile Ser Val Leu Gly Ser Asn Gly
785                 790                 795                 800

Thr Pro Trp Gly Ser Asn Ala Val Leu Gly Ser Glu Val Leu Lys Lys
                805                 810                 815

Ile Ala Met Ala Lys Gly Lys Ser Val Ala Gln Val Ser Met Arg Trp
                820                 825                 830

Val Tyr Glu Gln Gly Ala Ser Leu Val Val Lys Ser Phe Ser Glu Glu
        835                 840                 845

Arg Leu Arg Glu Asn Leu Asn Ile Phe Asp Trp Glu Leu Thr Lys Glu
        850                 855                 860

Asp His Glu Lys Ile Gly Glu Ile Pro Gln Cys Arg Ile Leu Ser Ala
865                 870                 875                 880

Tyr Phe Leu Val Ser Pro Asn Gly Pro Phe Lys Ser Gln Glu Glu Leu
                885                 890                 895

Trp Asp Asp Glu Ala
            900

<210> SEQ ID NO 10
<211> LENGTH: 32
<212> TYPE: PRT
<213> ORGANISM: Papaver somniferum

<400> SEQUENCE: 10

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

<210> SEQ ID NO 11
<211> LENGTH: 548
<212> TYPE: PRT
<213> ORGANISM: Papaver somniferum

<400> SEQUENCE: 11

Arg Lys Thr Phe Leu Asn Asn Tyr Ser Ser Pro Ala Ser Ser Thr
1               5                   10                  15

Lys Thr Ala Val Leu Ser His Gln Arg Gln Gln Ser Cys Ala Leu Pro
            20                  25                  30

Ile Ser Gly Leu Leu His Ile Phe Met Asn Lys Asn Gly Leu Ile His
            35                  40                  45

Val Thr Leu Gly Asn Met Ala Asp Lys Tyr Gly Pro Ile Phe Ser Phe
50                  55                  60

Pro Thr Gly Ser His Arg Thr Leu Val Val Ser Ser Trp Glu Met Val
65                  70                  75                  80

Lys Glu Cys Phe Thr Gly Asn Asn Asp Thr Ala Phe Ser Asn Arg Pro
                85                  90                  95

Ile Pro Leu Ala Phe Lys Thr Ile Phe Tyr Ala Cys Gly Gly Ile Asp
                100                 105                 110

Ser Tyr Gly Leu Ser Ser Val Pro Tyr Gly Lys Tyr Trp Arg Glu Leu
            115                 120                 125

Arg Lys Val Cys Val His Asn Leu Leu Ser Asn Gln Gln Leu Leu Lys
        130                 135                 140
```

```
Phe Arg His Leu Ile Ile Ser Gln Val Asp Thr Ser Phe Asn Lys Leu
145                 150                 155                 160

Tyr Glu Leu Cys Lys Asn Ser Glu Asp Asn His Gly Asn Tyr Thr Thr
                165                 170                 175

Thr Thr Thr Thr Ala Ala Gly Met Val Arg Ile Asp Asp Trp Leu Ala
            180                 185                 190

Glu Leu Ser Phe Asn Val Ile Gly Arg Ile Val Cys Gly Phe Gln Ser
        195                 200                 205

Gly Pro Lys Thr Gly Ala Pro Ser Arg Val Glu Gln Phe Lys Glu Ala
    210                 215                 220

Ile Asn Glu Ala Ser Tyr Phe Met Ser Thr Ser Pro Val Ser Asp Asn
225                 230                 235                 240

Val Pro Met Leu Gly Trp Ile Asp Gln Leu Thr Gly Leu Thr Arg Asn
                245                 250                 255

Met Lys His Cys Gly Lys Lys Leu Asp Leu Val Val Glu Ser Ile Ile
            260                 265                 270

Asn Asp His Arg Gln Lys Arg Arg Phe Ser Arg Thr Lys Gly Gly Asp
        275                 280                 285

Glu Lys Asp Asp Glu Gln Asp Asp Phe Ile Asp Ile Cys Leu Ser Ile
    290                 295                 300

Met Glu Gln Pro Gln Leu Pro Gly Asn Asn Asn Pro Ser Gln Ile Pro
305                 310                 315                 320

Ile Lys Ser Ile Val Leu Asp Met Ile Gly Gly Gly Thr Asp Thr Thr
                325                 330                 335

Lys Leu Thr Thr Ile Trp Thr Leu Ser Leu Leu Leu Asn Asn Pro His
            340                 345                 350

Val Leu Asp Lys Ala Lys Gln Glu Val Asp Ala His Phe Arg Thr Lys
        355                 360                 365

Arg Arg Ser Thr Asn Asp Ala Ala Ala Val Val Asp Phe Asp Asp
    370                 375                 380

Ile Arg Asn Leu Val Tyr Ile Gln Ala Ile Ile Lys Glu Ser Met Arg
385                 390                 395                 400

Leu Tyr Pro Ala Ser Pro Val Val Glu Arg Leu Ser Gly Glu Asp Cys
                405                 410                 415

Val Val Gly Gly Phe His Val Pro Ala Gly Thr Arg Leu Trp Ala Asn
            420                 425                 430

Val Trp Lys Met Gln Arg Asp Pro Lys Val Trp Asp Pro Leu Val
        435                 440                 445

Phe Arg Pro Asp Arg Phe Leu Ser Asp Glu Gln Lys Met Val Asp Val
    450                 455                 460

Arg Gly Gln Asn Tyr Glu Leu Leu Pro Phe Gly Ala Gly Arg Arg Val
465                 470                 475                 480

Cys Pro Gly Val Ser Phe Ser Leu Asp Leu Met Gln Leu Val Leu Thr
                485                 490                 495

Arg Leu Ile Leu Glu Phe Glu Met Lys Ser Pro Ser Gly Lys Val Asp
            500                 505                 510

Met Thr Ala Thr Pro Gly Leu Met Ser Tyr Lys Val Ile Pro Leu Asp
        515                 520                 525

Ile Leu Leu Thr His Arg Arg Ile Lys Pro Cys Val Gln Ser Ala Ala
    530                 535                 540

Ser Glu Arg Asp
545
```

-continued

```
<210> SEQ ID NO 12
<211> LENGTH: 321
<212> TYPE: PRT
<213> ORGANISM: Papaver somniferum

<400> SEQUENCE: 12

Met Glu Ser Ser Gly Val Pro Val Ile Thr Leu Gly Ser Gly Lys Val
1               5                   10                  15

Met Pro Val Leu Gly Met Gly Thr Phe Glu Lys Val Gly Lys Gly Ser
            20                  25                  30

Glu Arg Glu Arg Leu Ala Ile Leu Lys Ala Ile Glu Val Gly Tyr Arg
        35                  40                  45

Tyr Phe Asp Thr Ala Ala Tyr Glu Thr Glu Val Leu Gly Glu
    50                  55                  60

Ala Ile Ala Glu Ala Leu Gln Leu Gly Leu Val Lys Ser Arg Asp Glu
65                  70                  75                  80

Leu Phe Ile Ser Ser Met Leu Trp Cys Thr Asp Ala His Ala Asp Arg
                85                  90                  95

Val Leu Leu Ala Leu Gln Asn Ser Leu Arg Asn Leu Lys Leu Glu Tyr
                100                 105                 110

Val Asp Leu Tyr Met Leu Pro Phe Pro Ala Ser Leu Lys Pro Gly Lys
            115                 120                 125

Ile Thr Met Asp Ile Pro Glu Glu Asp Ile Cys Arg Met Asp Tyr Arg
        130                 135                 140

Ser Val Trp Ala Ala Met Glu Glu Cys Gln Asn Leu Gly Phe Thr Lys
145                 150                 155                 160

Ser Ile Gly Val Ser Asn Phe Ser Cys Lys Lys Leu Gln Glu Leu Met
                165                 170                 175

Ala Thr Ala Asn Ile Pro Pro Ala Val Asn Gln Val Glu Met Ser Pro
            180                 185                 190

Ala Phe Gln Gln Lys Lys Leu Arg Glu Tyr Cys Asn Ala Asn Asn Ile
        195                 200                 205

Leu Val Ser Ala Ile Ser Val Leu Gly Ser Asn Gly Thr Pro Trp Gly
210                 215                 220

Ser Asn Ala Val Leu Gly Ser Glu Val Leu Lys Lys Ile Ala Met Ala
225                 230                 235                 240

Lys Gly Lys Ser Val Ala Gln Val Ser Met Arg Trp Val Tyr Glu Gln
                245                 250                 255

Gly Ala Ser Leu Val Val Lys Ser Phe Ser Glu Glu Arg Leu Arg Glu
            260                 265                 270

Asn Leu Asn Ile Phe Asp Trp Glu Leu Thr Lys Glu Asp His Glu Lys
        275                 280                 285

Ile Gly Glu Ile Pro Gln Cys Arg Ile Leu Ser Ala Tyr Phe Leu Val
    290                 295                 300

Ser Pro Asn Gly Pro Phe Lys Ser Gln Glu Glu Leu Trp Asp Asp Glu
305                 310                 315                 320

Ala
```